US010677772B2

(12) United States Patent
Mou et al.

(10) Patent No.: US 10,677,772 B2
(45) Date of Patent: *Jun. 9, 2020

(54) INFORMATION TRANSMITTING SYSTEM FOR ACTUATING AND SENSING MODULE

(71) Applicant: Microjet Technology Co., Ltd., Hsinchu (TW)

(72) Inventors: Hao-Jan Mou, Hsinchu (TW); Chi-Feng Huang, Hsinchu (TW); Yung-Lung Han, Hsinchu (TW); Chang-Yen Tsai, Hsinchu (TW); Wei-Ming Lee, Hsinchu (TW); Hsuan-Kai Chen, Hsinchu (TW)

(73) Assignee: MICROJET TECHNOLOGY CO., LTD., Hsinchu (TW)

(*) Notice: Subject to any disclaimer, the term of this patent is extended or adjusted under 35 U.S.C. 154(b) by 0 days.

This patent is subject to a terminal disclaimer.

(21) Appl. No.: 16/014,609

(22) Filed: Jun. 21, 2018

(65) Prior Publication Data

US 2019/0033280 A1    Jan. 31, 2019

(30) Foreign Application Priority Data

Jul. 27, 2017    (TW) .............................. 106125328 A

(51) Int. Cl.
*G08B 21/00*    (2006.01)
*G01N 33/00*    (2006.01)
(Continued)

(52) U.S. Cl.
CPC ..... *G01N 33/0075* (2013.01); *G01N 33/0031* (2013.01); *G08B 21/12* (2013.01);
(Continued)

(58) Field of Classification Search
CPC .......... G01N 33/0031; G01N 33/0075; G08B 21/12; G08B 21/14; G08C 17/00; H04L 67/125
See application file for complete search history.

(56) References Cited

U.S. PATENT DOCUMENTS 9,593,861 B1 *    3/2017    Burnett .................... F24F 11/30
2008/0045156 A1 *    2/2008    Sakhpara ........... G01N 33/0063
455/67.11
(Continued)

FOREIGN PATENT DOCUMENTS

TW    201337262 A    9/2013
TW    M525446 U    7/2016
TW    M527089 U    8/2016

*Primary Examiner* — Mark S Rushing
(74) *Attorney, Agent, or Firm* — Birch, Stewart, Kolasch & Birch, LLP

(57) ABSTRACT

An information transmitting system for an actuating and sensing module includes an actuating and sensing device and a connection device. The actuating and sensing device includes a sensor, an actuating device, a microprocessor and a data transceiver. After a monitored data sensed by the at least one sensor is transmitted to the microprocessor, the monitored data is processed into an output data by the microprocessor. After the output data is received by the data transceiver, the output data is transmitted from the data transceiver to the connection device. After a control command from the connection device is received by the data transceiver, the control command is transmitted to the microprocessor to control the sensor and the actuating device.

19 Claims, 9 Drawing Sheets

(51) Int. Cl.
*H04L 29/08* (2006.01)
*G08C 17/00* (2006.01)
*G08B 21/14* (2006.01)
*G08B 21/12* (2006.01)

(52) U.S. Cl.
CPC .............. *G08B 21/14* (2013.01); *G08C 17/00* (2013.01); *H04L 67/125* (2013.01)

(56) References Cited

U.S. PATENT DOCUMENTS

| | | | |
|---|---|---|---|
| 2015/0052975 A1* | 2/2015 | Martin | G01N 33/00 73/31.02 |
| 2015/0153299 A1* | 6/2015 | Chou | G01N 33/0075 205/775 |
| 2017/0314804 A1* | 11/2017 | Kannan | G05B 15/02 |

* cited by examiner

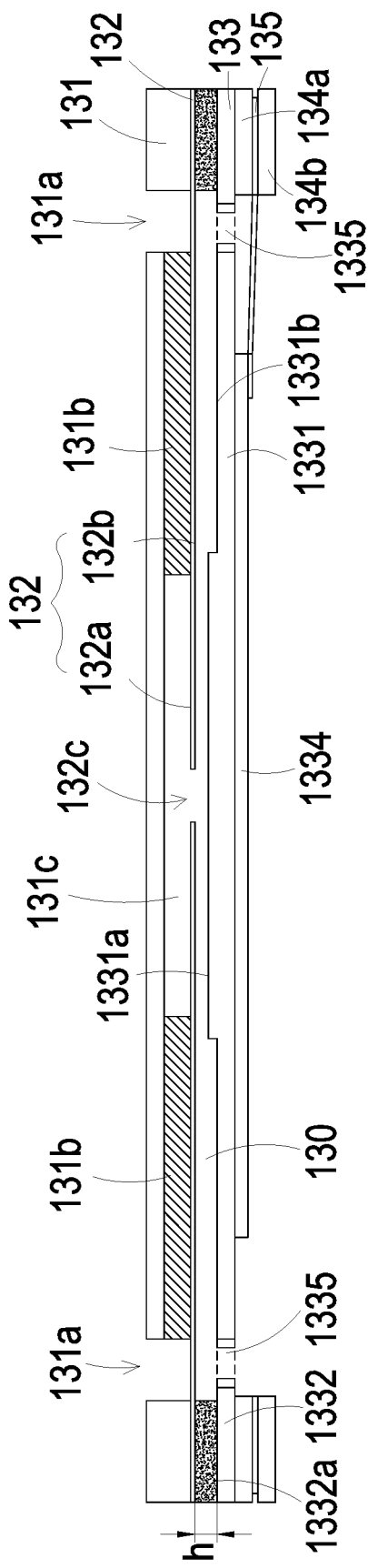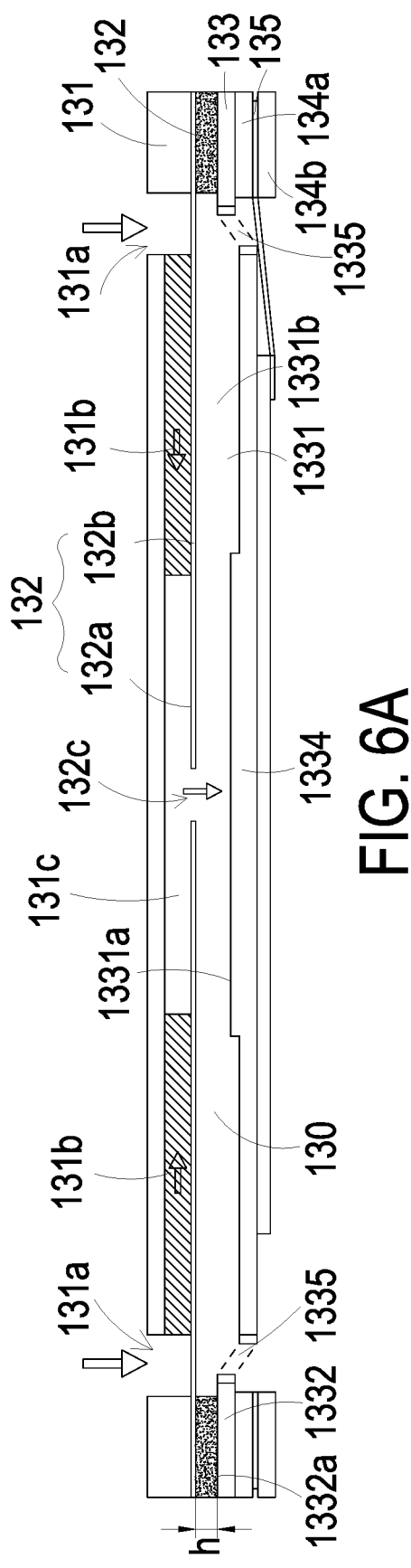

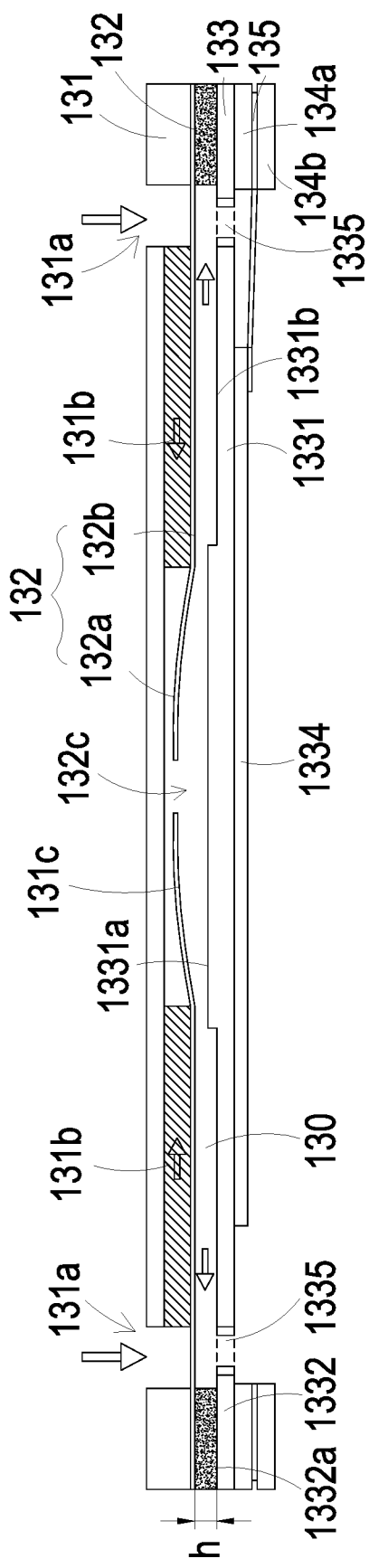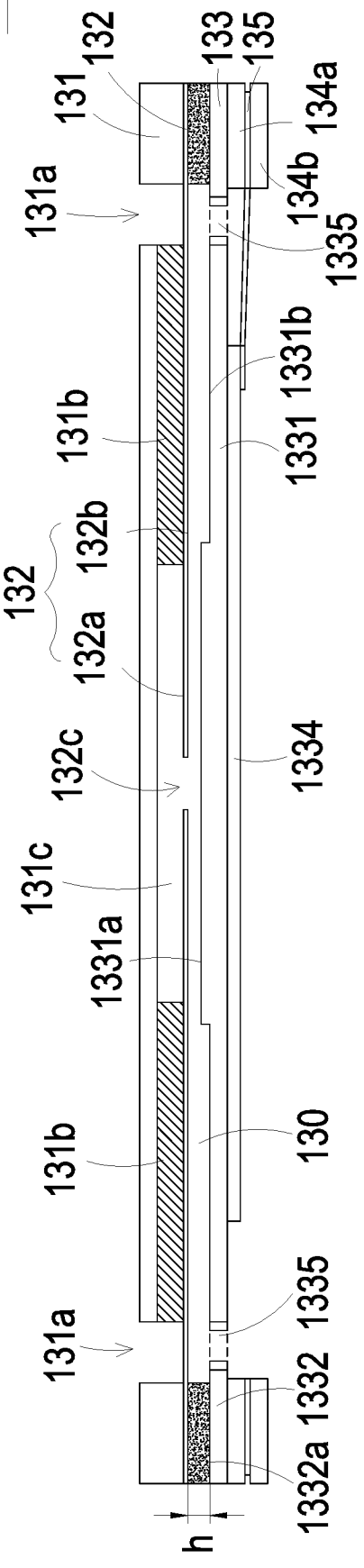

INFORMATION TRANSMITTING SYSTEM FOR ACTUATING AND SENSING MODULE

FIELD OF THE INVENTION

The present disclosure relates to an actuating and sensing module utilizing in environmental monitoring, and more particularly to an information transmitting system for an actuating and sensing module.

BACKGROUND OF THE INVENTION

Nowadays, people pay much attention to monitoring environmental air quality in daily living, e.g., monitoring carbon monoxide, carbon dioxide, volatile organic compounds (VOC), PM2.5, and so on. The exposure of these gases or substances in the environment can cause human health problems or can even harm the life. Therefore, it has become an important issue for every country to develop and implement environmental air quality monitoring technology.

Generally, it is feasible to use a sensor to monitor the air quality in the environment. If the sensor can further provide immediate monitored information for the people in the environment, the people can be alerted to take precautions or escape promptly, thus the negative influence on human body and injury to the health caused by the exposure to the harmful gas are prevented. In this regard, the sensor is suitably used for monitoring the environment.

Regarding using the sensor to monitor the environment and provide related data to the user, the monitoring sensitivity and the precision of the sensor should be taken into consideration. If the air in the environment is transferred to the sensor through natural convection, the flowrate of the airflow to be received by the sensor is usually not stable. Under this circumstance, the result of monitoring the environment is not accurate. Moreover, since the airflow is transferred to the sensor through natural convection, the response time of the sensor is long. In other words, the real-time monitoring efficacy is low.

Nowadays, there are large-scale environmental monitoring base stations provided to monitor environmental air quality. However, those base stations are only suitable for monitoring air quality in a large area, which are unable to promptly monitor the quality of the air surrounding a human being with precision and efficiency, e.g., the indoor air quality or the ambient air close to the human being. If the sensor is integrated into a portable electronic device, the air quality can be real-time monitored in everywhere and at any time. Moreover, the monitored data can be transmitted to a cloud database in real time for database construction and data integration. Consequently, the monitored data of the air quality can be more accurately and immediately provided for enabling an air quality notification mechanism and an air quality processing mechanism.

Therefore, there is a need of providing an information transmitting system for an actuating and sensing module for increasing the monitoring accuracy of the sensor, increasing the monitoring speed of the sensor, immediately monitoring the air quality in everywhere and at any time, transmitting the monitored data to the cloud database for fetching more accurate and prompt air quality information, and enabling the air quality notification mechanism and the air quality processing mechanism according to the air quality information.

SUMMARY OF THE INVENTION

An object of the present disclosure provides an information transmitting system for an actuating and sensing module. The system includes an actuating and sensing device and a connection device. The actuating and sensing device includes at least one sensor, at least one actuating device, a microprocessor, and a data transceiver which are integrated as a modular structure. The actuating device is used for driving the fluid to flow at a stable flowrate, so that the sensor is provided with the fluid flow in consistent amount and can directly sense the fluid in shorter response time. Therefore, the sensor acquires accurate and precise sensing results. Moreover, a data transceiver receives a control command to enable the sensor and the actuating device. After a monitored data sensed by the at least one sensor is transmitted to the microprocessor, the monitored data is processed into an output data by the microprocessor. The output data is transmitted to the connection device to be displayed, stored and transmitted thereby. Consequently, the purpose of immediately displaying the monitoring information and issuing the notification signal are achieved. Furthermore, the output data can be transmitted to a cloud database for database construction and data integration. Consequently, the more immediate and accurate air quality information is provided for enabling an air quality notification mechanism and an air quality processing mechanism.

Another object of the present disclosure provides an information transmitting system for an actuating and sensing module, in which the actuating and sensing device is not necessarily equipped with a power source because it has a power controller which receives energy from the power supply device, by which the sensor and the actuating device are powered. Therefore, the installation space of the overall modular structure is saved, and the purpose of minimizing the modular structure is achieved, so that the modular structure is suitably applied to an electronic device for monitoring the air quality.

In accordance with an aspect of the present disclosure, an information transmitting system for an actuating and sensing module is provided. The system includes an actuating and sensing device and a connection device. The actuating and sensing device includes at least one sensor, at least one actuating device, a microprocessor and a data transceiver. After a monitored data sensed by the at least one sensor is transmitted to the microprocessor, the monitored data is processed into an output data by the microprocessor. The output data is received by the data transceiver, and the output data is transmitted from the data transceiver to the connection device. A control command from the connection device is received by the data transceiver, and the control command is transmitted to the microprocessor. According to the control command, the at least one sensor and the at least one actuating device are enabled to perform operations.

The above contents of the present disclosure will become more readily apparent to those ordinarily skilled in the art after reviewing the following detailed description and accompanying drawings, in which:

BRIEF DESCRIPTION OF THE DRAWINGS

FIG. 5 is a schematic cross-sectional view illustrating the fluid actuating device as shown in FIGS. 3A and 3B; and FIGS. 6A to 6E schematically illustrate the actions of the fluid actuating device of the actuating and sensing device according to the embodiment of the present disclosure.

DETAILED DESCRIPTION OF THE PREFERRED EMBODIMENT

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1A:
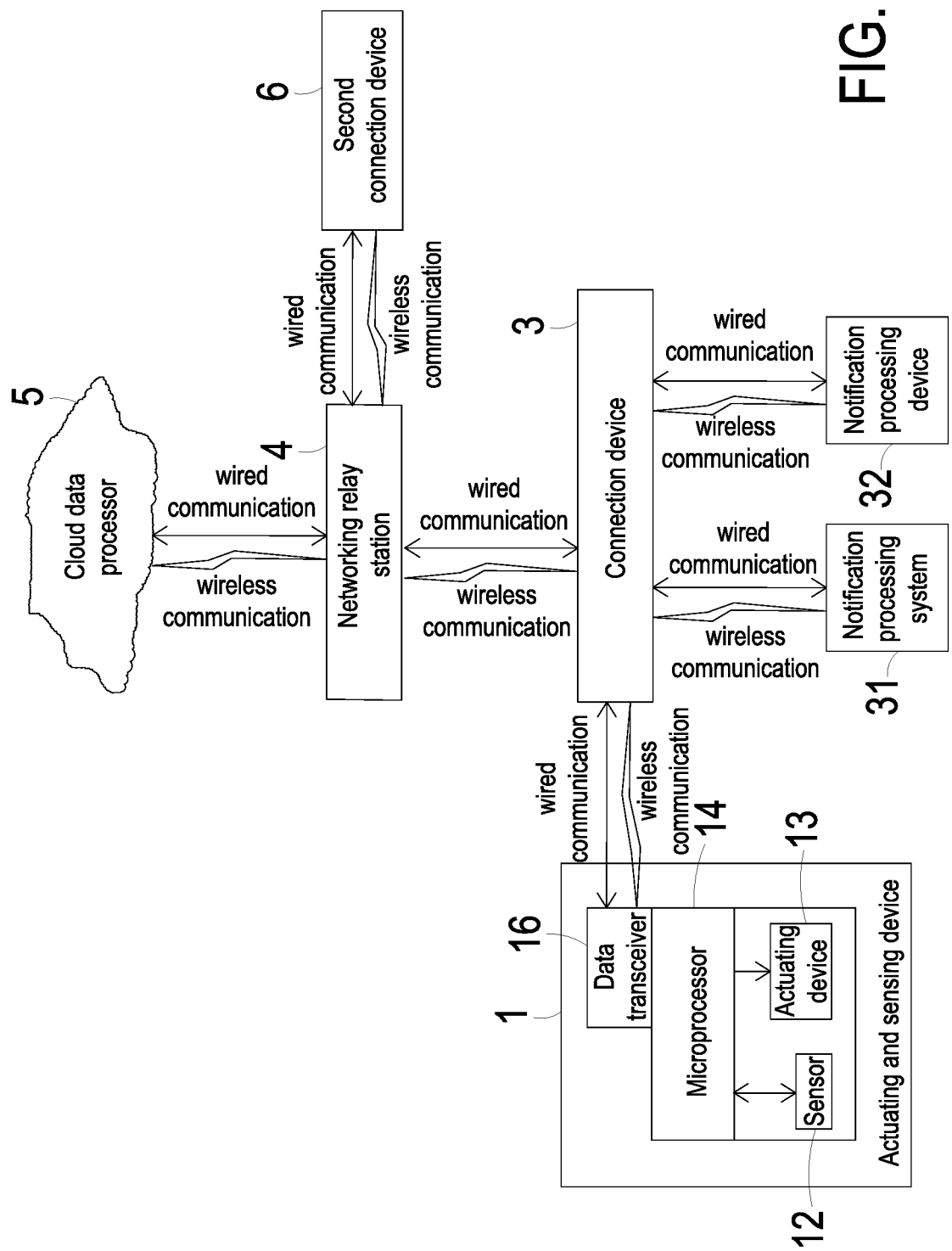
FIG. 1A schematically illustrates the architecture of an information transmitting system for an actuating and sensing module according to a first embodiment of the present disclosure.
Figure 1B:
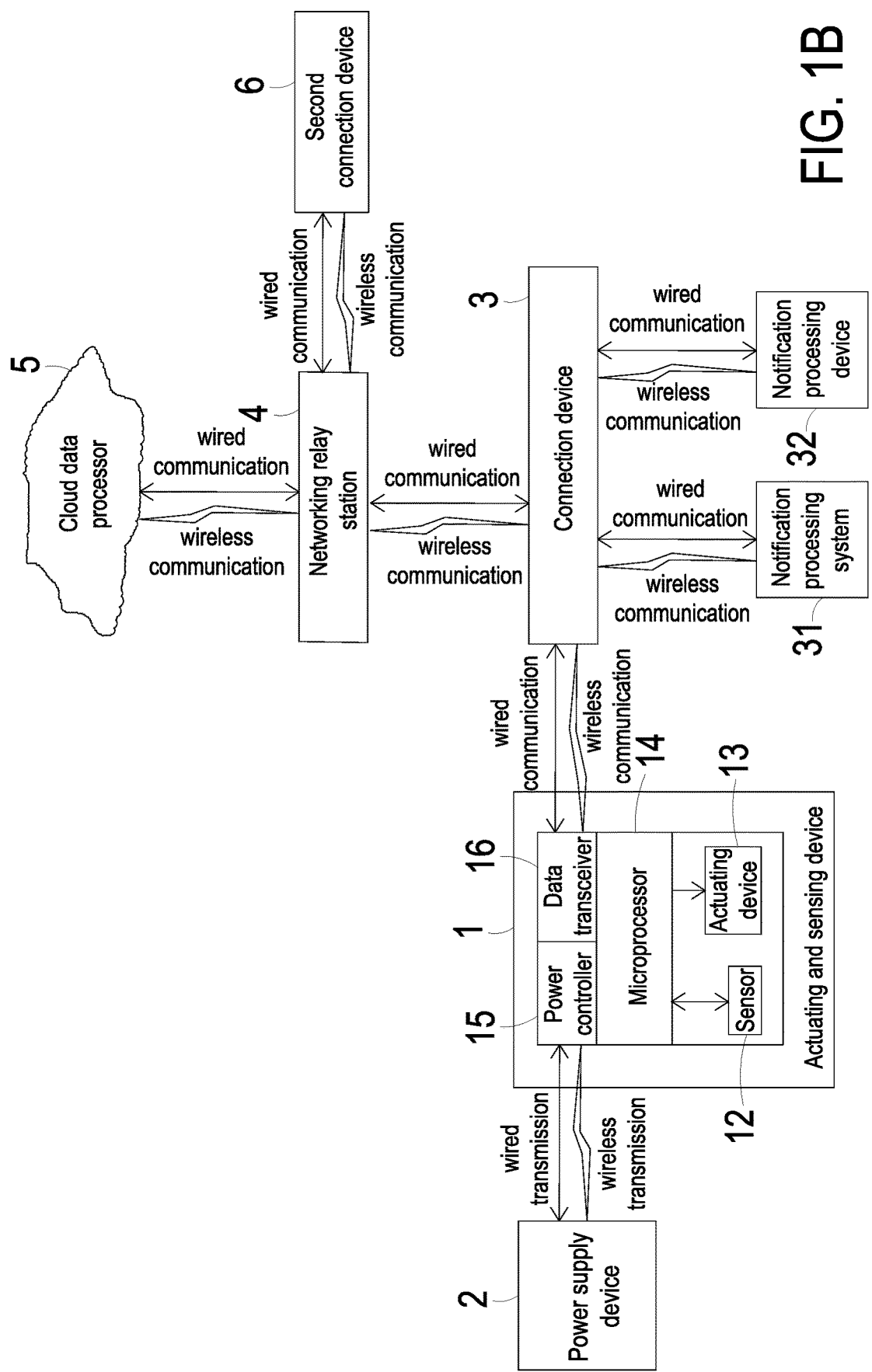
FIG. 1B schematically illustrates the architecture of an information transmitting system for an actuating and sensing module according to a second embodiment of the present disclosure.

Please refer to FIGS. 1A and 1B. The present discourse provides an information transmitting system for an actuating and sensing module, in which the information transmitting system includes at least one actuating and sensing device 1, at least one sensor 12, at least one actuating device 13, at least one microprocessor 14, at least one data transceiver 16, at least one connection device 3, at least one output data, and at least one control command. The number of the actuating and sensing device 1, the sensor 12, the actuating device 13, the microprocessor 14, the data transceiver 16, the connection device 3, the output data and the control command is exemplified by one for each in the following embodiments but not limited thereto. It is noted that each of the actuating and sensing device 1, the sensor 12, the actuating device 13, the microprocessor 14, the data transceiver 16, the connection device 3, the output data and the control command can also be provided in plural numbers.

Please refer to FIG. 1A. FIG. 1A schematically illustrates the architecture of an information transmitting system for an actuating and sensing module according to a first embodiment of the present disclosure. The information transmitting system for the actuating and sensing module includes an actuating and sensing device 1 and a connection device 3. The actuating and sensing device 1 includes at least one sensor 12, at least one actuating device 13, a microprocessor 14 and a data transceiver 16. The data transceiver 16 can receive or transmit data.

An example of the sensor 12 includes but is not limited to a temperature sensor, a volatile organic compound sensor (e.g., a sensor for measuring formaldehyde or ammonia gas), a particulate sensor (e.g., a PM2.5 particle sensor), a carbon monoxide sensor, a carbon dioxide sensor, an oxygen sensor, an ozone sensor, any other appropriate gas sensor, a humidity sensor, a water content sensor, a substance sensor (e.g., a sensor for measuring compounds or biological substances in liquid or air), a water quality sensor, any other appropriate liquid sensor, a light sensor, or the combination thereof.

In an embodiment, when the actuating device 13 is enabled to drive a fluid to pass through the sensor 12, the fluid is guided to the sensor 12 at a stable flowrate. Consequently, the sensor 12 can monitor the fluid directly to acquire the accurate result. Moreover, since the response time of the sensor 12 is reduced, the efficiency of monitoring the fluid is enhanced. The fluid may be a gas or a liquid, but not limited thereto.

The sensor 12 is used for monitoring the environment to acquire a monitored data. The microprocessor 14 processes and converts the monitored data transmitted from the sensor 12 into an output data. The microprocessor 14 transmits the output data to the data transceiver 16, and the output data is transmitted from the data transceiver 16 to the connection device 3. Consequently, the information carried by the output data can be displayed and stored by the connection device 3. The output data may be stored in a storage device (not shown) of the connection device 3. In an embodiment, the connection device 3 is in communication with a notification processing system 31 to actively (i.e. directly notify) or passively (i.e. operated by a user to whom the information carried by the output data is provided) enable an air quality notification mechanism. For example, an instant air quality map informs people to avoid away or wear masks. In some other embodiments, the connection device 3 is in communication with a notification processing device 32 to actively (i.e. directly operate) or passively (i.e. operated by a user to whom the information carried by the output data is provided) enable an air quality processing mechanism. For example, an air cleaner or an air-conditioner is enabled to filter the air and improve air quality.

The connection device 3 may be a display device with a wired communication module (e.g., a desktop computer), a display device with a wireless communication module (e.g., a notebook computer), or a portable electronic device with a wireless communication module (e.g., a mobile phone). For example, the wired communication module has an RS485 communication port, an RS232 communication port, a Modbus communication port or a KNX communication port, and the wireless communication module perfoinis a wireless communication process according to a Zigbee communication technology, a Z-wave communication technology, an RF communication technology, a Bluetooth communication technology, a Wifi communication technology or an EnOcean communication technology.

In some embodiments, the information transmitting system for the actuating and sensing module further comprises a networking relay station 4 and a cloud data processor 5. The connection device 3 sends the information carried by the output data to the networking relay station 4, after which the networking relay station 4 sends the information carried by the output data to the cloud data processor 5 to make it stored in and processed by the cloud data processor 5. The cloud data processor 5 processes the information carried by the output data to correspondingly issue a notification signal to the connection device 3 through the networking relay station 4. After the connection device 3 receives the notification signal, the notification processing system 31 connected with the connection device 3 receives the notification signal from the connection device 3, and accordingly enables an air quality notification mechanism. Alternatively, the notification processing device 32 connected with the connection device 3 receives the notification signal from the connection device 3, and accordingly enables an air quality processing mechanism.

In an embodiment, the connection device 3 issues a control command to the actuating and sensing device 1 so as to control the operation of the actuating and sensing device 1. The control command may be transmitted to the data transceiver 16 in the wired or wireless communication transmission manner as discussed above. Then, the control command is transmitted to the microprocessor 14 to control the sensor 12 to perform the sensing operation and enable the actuating device 13.

In some embodiments, the information transmitting system for the actuating and sensing module further includes a second connection device 6 for issuing a control command to the cloud data processor 5 through the networking relay station 4. Then the control command is transmitted from the cloud data processor 5 to the connection device 3 through the networking relay station 4. Afterwards, the control command is transmitted by the connection device 3 to the data transceiver 16 of the actuating and sensing module 1. Then, the data transceiver 16 transmits the control command to the microprocessor 14. According to the control command, the microprocessor 14 enables the sensor 12 to perform the sensing operation and enables the actuating device 13. In these embodiments, the second connection device 6 may be a device with a wired communication transmission module, a device with a wireless communication transmission module, or a portable electronic device with a wireless communication transmission module, but not limited thereto.

The actuating device 13 is a driving device capable of driving an operated system in response to a control signal. An example of the actuating device 13 includes but is not limited to an electric actuating device, a magnetic actuating device, a thermal actuating device, a piezoelectric actuating device, and a fluid actuating device. For example, the electric actuating device is an electric actuating device of a DC motor, an AC motor or a step motor, the magnetic actuating device is an magnetic actuating device of a magnetic coil motor, the thermal actuating device is a thermal actuating device of a heat pump, the piezoelectric actuating device is a piezoelectric actuating device of a piezoelectric pump, and the fluid actuating device is a fluid actuating device of a gas pump or a liquid pump.

Figure 2:
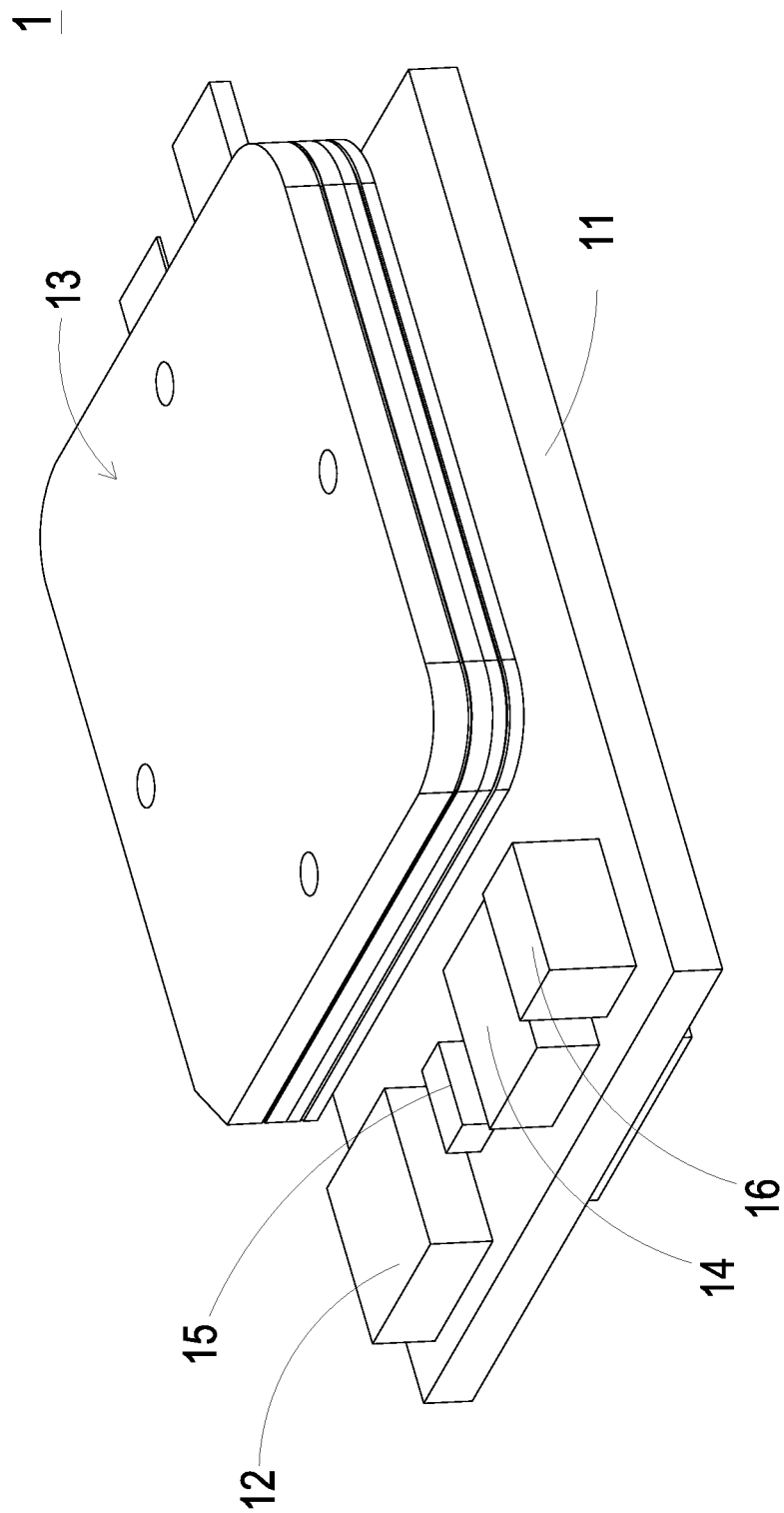
FIG. 2 is a schematic perspective view illustrating the structure of an actuating and sensing device of the information transmitting system for the actuating and sensing module according to an embodiment of the present disclosure.

Please refer to FIG. 2. FIG. 2 is a schematic perspective view illustrating the structure of an actuating and sensing device of the information transmitting system for the actuating and sensing module according to an embodiment of the present disclosure. The actuating and sensing device 1 further includes a carrier 11. The at least one sensor 12, the at least one actuating device 13, the microprocessor 14, the power controller 15 and the data transceiver 16 are mounted on the carrier 11 to be integrated into a modular structure. In some embodiments, the carrier 11 is a substrate such as a printed circuit board (PCB). The sensor 12 and the fluid actuating device 13 are disposed on the carrier 11 in an array arrangement. In some other embodiments, the carrier 11 is an application-specific integrated circuit (ASIC). In further other embodiments, the carrier 11 is a system on chip (SOC), wherein the sensor 12 is deposited on the carrier 11 and the actuating device 13 is packaged on the carrier 11. That is, the carrier 11, the sensor 12 and the actuating device 13 are combined together as an integral structure. The profile and type of the carrier 11 are not restricted. Any platform for supporting the sensor 12 and the actuating device 13 can be used as the carrier 11.

Figure 3A:
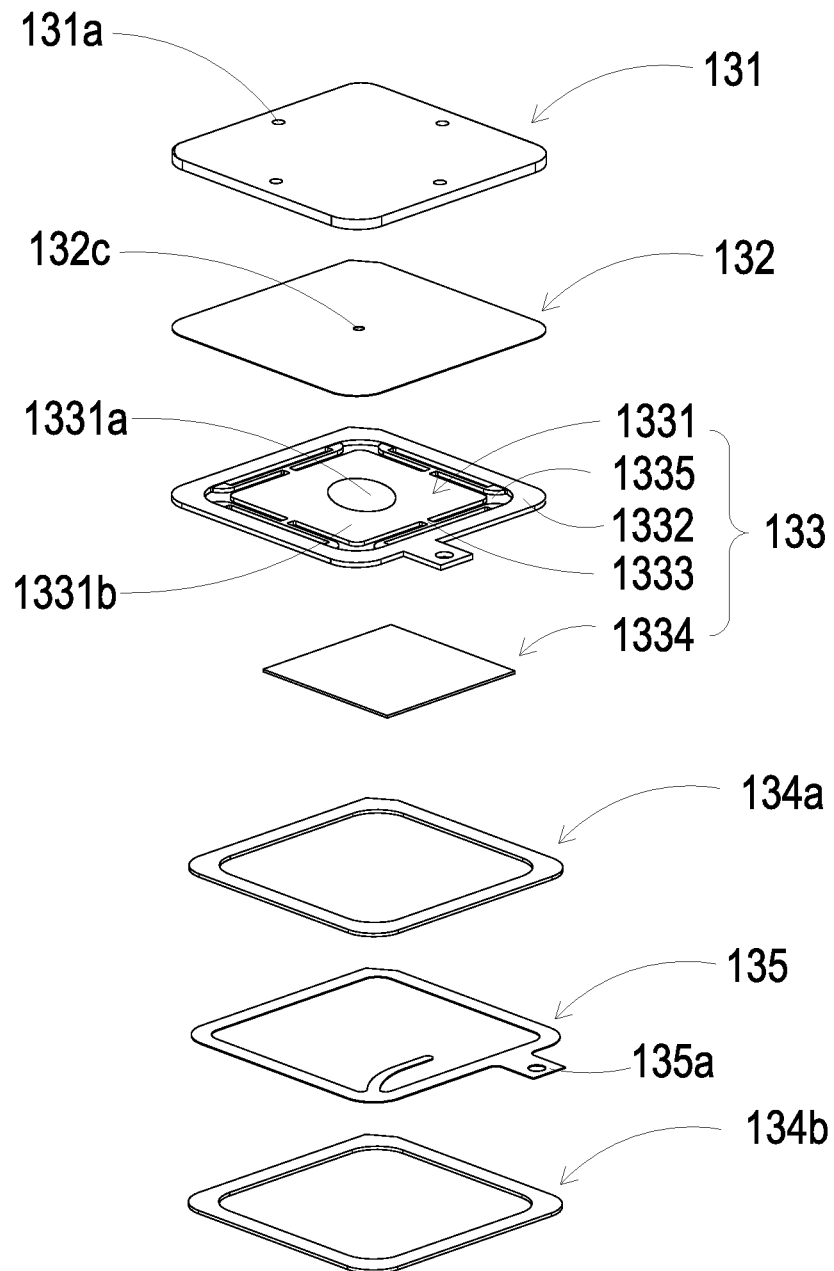
FIG. 3A is a schematic exploded view illustrating a fluid actuating device used in the actuating and sensing device of the present disclosure.
Figure 3B:
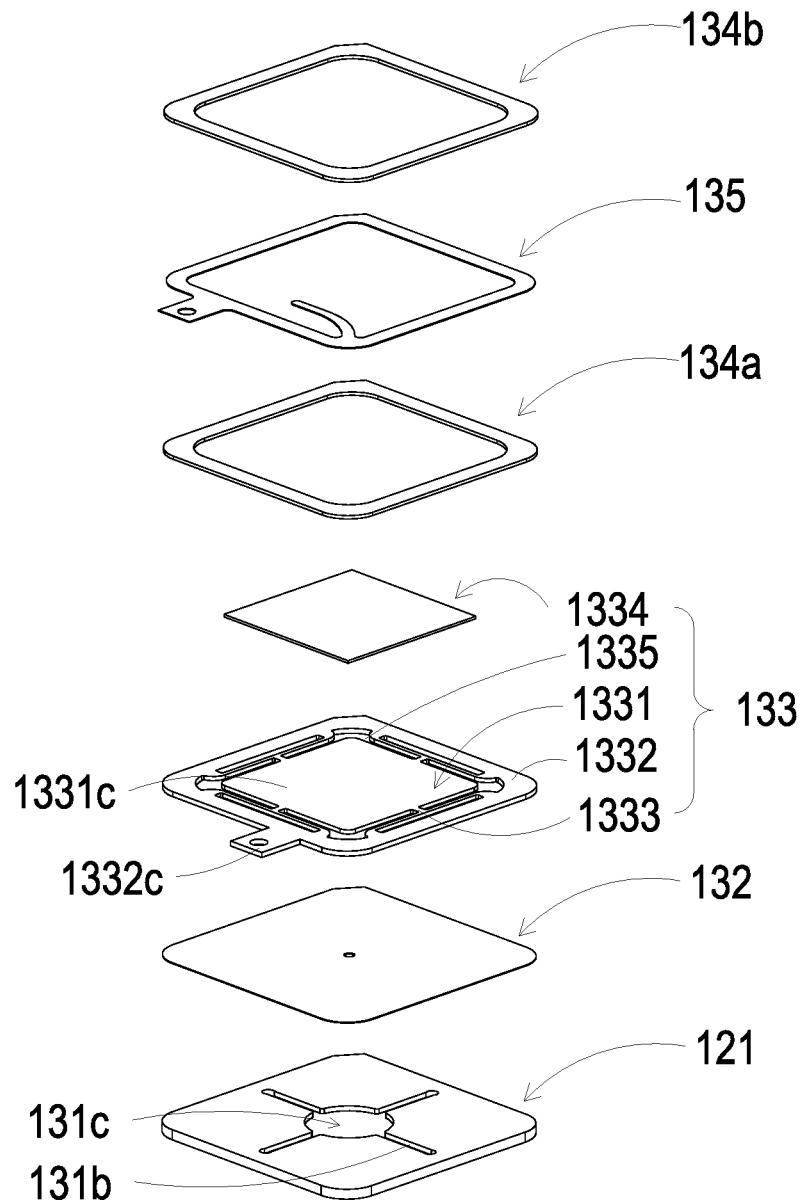
FIG. 3B is a schematic exploded view illustrating the fluid actuating device of FIG. 3A and taken along another viewpoint.

Please refer to FIGS. 3A and 3B. In the following description, the actuating device 13 is exemplified by a fluid actuating device. Preferably but not exclusively, the fluid actuating device 13 is a driving structure of a piezoelectric pump or a driving structure of a micro-electro-mechanical system (MEMS) pump. Hereinafter, the actions of the fluid actuating device 13 are exemplified by the driving structure of a piezoelectric pump and will be described as follows.

As shown in FIGS. 3A and 3B, the fluid actuating device 13 includes a fluid inlet plate 131, a resonance plate 132, a piezoelectric actuator 133, a first insulation plate 134a, a conducting plate 135 and a second insulation plate 134b. The piezoelectric actuator 133 is disposed spatially corresponding to the resonance plate 132. The fluid inlet plate 131, the resonance plate 132, the piezoelectric actuator 133, the first insulation plate 134a, the conducting plate 135 and the second insulation plate 134b are stacked on each other sequentially to be assembled and the cross-sectional view of the resulting structure of the fluid actuating device 13 is shown in FIG. 5.

The fluid inlet plate 131 has at least one inlet 131a. Preferably but not exclusively, the fluid inlet plate 131 has four inlets 131a. The inlets 131a run through the fluid inlet plate 131. In response to the action of the atmospheric pressure, the fluid can be introduced into the fluid actuating device 13 through the at least one inlet 131a. Moreover, at least one convergence channel 131b is formed on a first surface of the fluid inlet plate 131, and is in communication with the at least one inlet 131a on a second surface of the fluid inlet plate 131. Moreover, a central cavity 131c is located at the intersection of the convergence channels 131b. The central cavity 131c is in communication with the at least one convergence channel 131b, such that the fluid entered by the at least one inlet 131a would be introduced into the at least one convergence channel 131b and is guided to the central cavity 131c. Consequently, the fluid can be transferred by the fluid actuating device 13. In this embodiment, the at least one inlet 131a, the at least one convergence channel 131b and the central cavity 131c of the fluid inlet plate 131 are integrally formed in one piece. The central cavity 131c is a convergence chamber for temporarily storing the fluid. Preferably but not exclusively, the fluid inlet plate 131 is made of a stainless steel. Moreover, the depth of the convergence chamber defined by the central cavity 131c is equal to the depth of the at least one convergence channel 131b. The resonance plate 132 is made of a flexible material. The resonance plate 132 comprises a central aperture 132c disposed corresponding to the central cavity 131c of the fluid inlet plate 131 for allowing the fluid to be transferred therethrough. Preferably but not exclusively, the resonance plate 132 is made of copper.

The piezoelectric actuator 133 includes a suspension plate 1331, an outer frame 1332, at least one bracket 1333 and a piezoelectric plate 1334. The piezoelectric plate 1334 is attached on a first surface 1331c of the suspension plate 1331. In response to an applied voltage, the piezoelectric plate 1334 would be subjected to a deformation. When the piezoelectric plate 1334 is subjected to the deformation, the suspension plate 1331 is driven to undergo a bending vibration. The at least one bracket 1333 is connected between the suspension plate 1331 and the outer frame 1332, while the two ends of the bracket 1333 are connected with the outer frame 1332 and the suspension plate 1331 respectively so that the bracket 1333 can elastically support the suspension plate 1331. At least one vacant space 1335 is formed between the bracket 1333, the suspension plate 1331 and the outer frame 1332. The at least one vacant space 1335 is in communication with a fluid channel for allowing the fluid to go through. The type of the suspension plate 1331 and the outer frame 1332 and the type and the number of the at least one bracket 1333 may be varied according to the practical requirements. The outer frame 1332 is arranged around the suspension plate 1331. Moreover, a conducting pin 1332c is protruded outwardly from the outer frame 1332 so as to be electrically connected with an external circuit (not shown).

Figure 4:
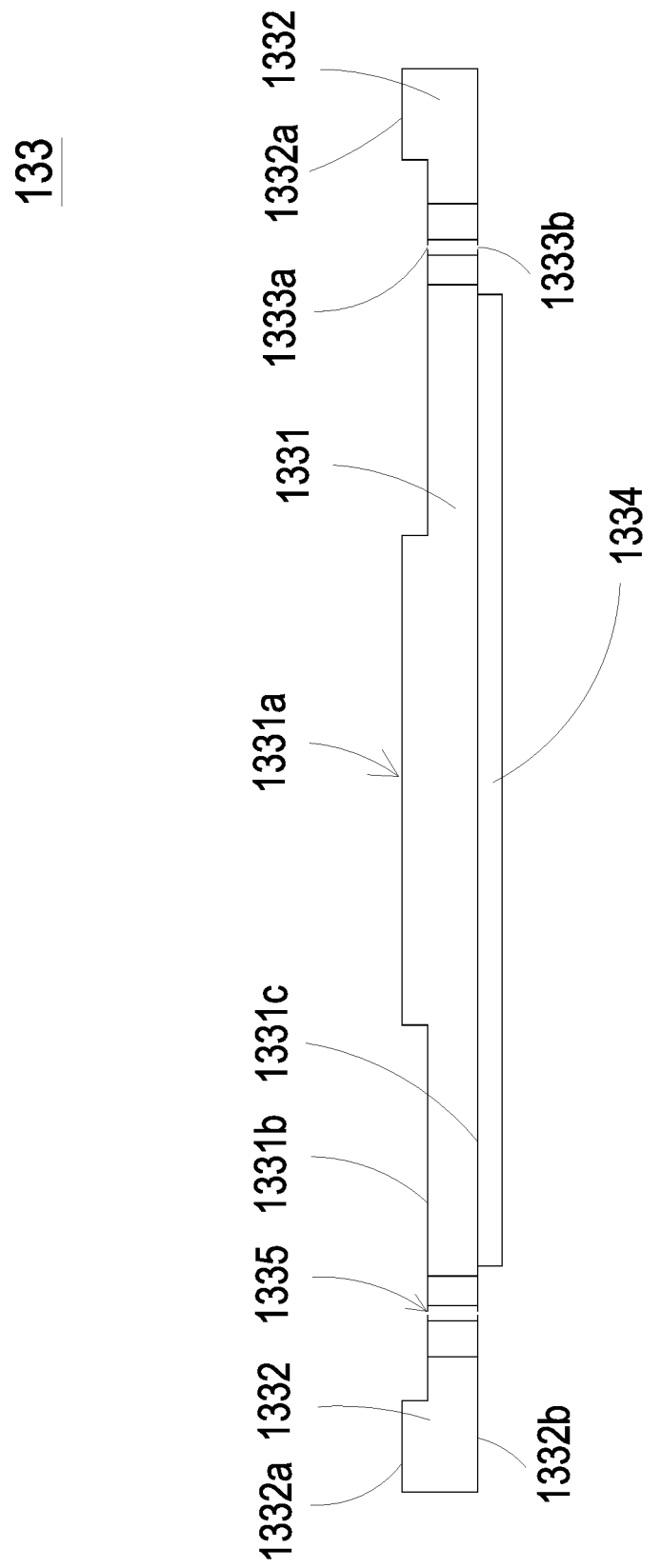
FIG. 4 is a schematic cross-sectional view illustrating the piezoelectric actuator of the fluid actuating device as shown in FIGS. 3A and 3B.

As shown in FIG. 4, the suspension plate 1331 has a bulge 1331a that makes the suspension plate 1331 a stepped structure. The bulge 1331a is formed on a second surface 1331b of the suspension plate 1331. The bulge 1331a may be a circular convex structure. A top surface of the bulge 1331a of the suspension plate 1331 is coplanar with a second surface 1332a of the outer frame 1332, while the second surface 1331b of the suspension plate 1331 is coplanar with a second surface 1333a of the bracket 1333. Moreover, there is a drop of specified amount from the bulge 1331a of the suspension plate 1331 (or the second surface 1332a of the outer frame 1332) to the second surface 1331b of the suspension plate 1331 (or the second surface 1333a of the bracket 1333). A first surface 1331c of the suspension plate 1331, a first surface 1332b of the outer frame 1332 and a first surface 1333b of the bracket 1333 are coplanar with each other. The piezoelectric plate 1334 is attached on the first surface 1331c of the suspension plate 1331. In some other embodiments, the suspension plate 1331 may be a square plate structure with two flat surfaces, but the type of the suspension plate 1331 may be varied according to the practical requirements. In this embodiment, the suspension plate 1331, the at least bracket 1333 and the outer frame 1332 are integrally formed and produced by using a metal plate (e.g., a stainless steel plate). In an embodiment, the length of a side of the piezoelectric plate 1334 is smaller than the length of a side of the suspension plate 1331. In another embodiment, the length of a side of the piezoelectric plate 1334 is equal to the length of a side of the suspension plate 1331. Similarly, the piezoelectric plate 1334 is a square plate structure to have the same shape as the suspension plate 1331.

Please refer to FIG. 3A. In an embodiment, in the fluid actuating device 13, the first insulation plate 134a, the conducting plate 135 and the second insulation plate 134b are stacked on each other sequentially and located under the piezoelectric actuator 133. The profiles of the first insulation plate 134a, the conducting plate 135 and the second insulation plate 134b substantially match the profile of the outer frame 1332 of the piezoelectric actuator 133. The first insulation plate 134a and the second insulation plate 134b are made of an insulating material (e.g. a plastic material) for providing insulating efficacy. The conducting plate 135 is made of an electrically conductive material (e.g. a metallic material) for providing electrically conducting efficacy. Moreover, the conducting plate 135 has a conducting pin 135a so as to be electrically connected with an external circuit (not shown).

Please refer to FIG. 5. In an embodiment, the fluid inlet plate 131, the resonance plate 132, the piezoelectric actuator 133, the first insulation plate 134a, the conducting plate 135 and the second insulation plate 134b of the fluid actuating device 13 are stacked on each other sequentially. Moreover, there is a gap h between the resonance plate 132 and the outer frame 1332 of the piezoelectric actuator 133, which is formed and maintained by a filler (e.g. a conductive adhesive) inserted therein in this embodiment. The gap h ensures the proper distance between the resonance plate 132 and the bulge 1331a of the suspension plate 1331 of the piezoelectric actuator 133, so that the fluid can be transferred quickly, the contact interference is reduced and the generated noise is largely reduced. In some embodiments, the height of the outer frame 1332 of the piezoelectric actuator 133 is increased, so that the gap is formed between the resonance plate 132 and the piezoelectric actuator 133.

Please refer to FIG. 3A, FIG. 3B and FIG. 5. After the fluid inlet plate 131, the resonance plate 132 and the piezoelectric actuator 133 are combined together, a movable part 132a and a fixed part 132b of the resonance plate 132 are defined, wherein the movable part 132a is located around the central aperture 132c. A convergence chamber for converging the fluid is defined by the movable part 132a of the resonance plate 132 and the fluid inlet plate 131 collaboratively. Moreover, a first chamber 130 is formed between the resonance plate 132 and the piezoelectric actuator 133 for temporarily storing the fluid. Through the central aperture 132c of the resonance plate 132, the first chamber 130 is in communication with the central cavity 131c of the fluid inlet plate 131. The peripheral regions of the first chamber 130 are in communication with the fluid channel through the vacant space 1335 between the brackets 1333 of the piezoelectric actuator 133.

Figure 6B:
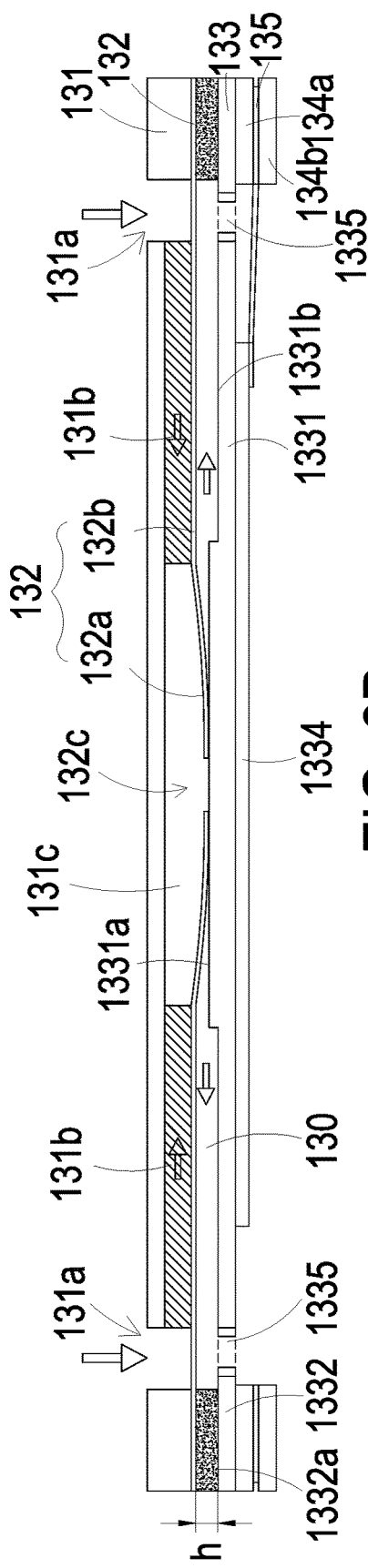

FIGS. 6A to 6E schematically illustrate the actions of the fluid actuating device of the actuating and sensing device according to the embodiment of the present disclosure. Please refer to FIG. 3A, FIG. 3B, FIG. 5 and FIGS. 6A to 6E. The actions of the fluid actuating device 13 will be described as follows. When the fluid actuating device 13 is enabled, the piezoelectric actuator 133 vibrates along a vertical direction in a reciprocating manner by using the bracket 1333 as a fulcrum. As shown in FIG. 6A, when the piezoelectric actuator 133 is vibrating downwardly in response to the applied voltage, the resonance between the piezoelectric actuator 133 and the resonance plate 132 occurs because the resonance plate 132 is light and thin. Due to the resonance, the resonance plate 132 also reciprocates vertically. That is, the region of the resonance plate 132 corresponding to the central cavity 131c of the fluid inlet plate 131, which is referred to as the movable part 132a, is subjected to a curvy deformation and driven to undergo bending vibration. Therefore, when the piezoelectric actuator 133 bends downwardly during vibration, the movable part 132a of the resonance plate 132 also bends downwardly because being pushed by the entering fluid and driven by the vibration of the piezoelectric actuator 133. In the meantime, the fluid is fed into the at least one inlet 131a of the fluid inlet plate 131, converged to the central cavity 131c of the fluid inlet plate 131 through the transportation by the at least one convergence channel 131b. Then, the fluid is transferred through the central aperture 132c of the resonance plate 132 which is disposed corresponding to the central cavity 131c, and introduced downwardly into the first chamber 130. Afterwards, being driven by the vibration of the piezoelectric actuator 133, the resonance between the piezoelectric actuator 133 and the resonance plate 132 occurs, and the resonance plate 132 also reciprocates vertically.

As shown in FIG. 6B, when the movable part 132a is vibrating downwardly, the movable part 132a moves down till abutting the bulge 1331a of the suspension plate 1331 of the piezoelectric actuator 133, so that the gap of the convergence chamber between the part of the suspension plate 1331 excluding the bulge 1331a and the fixed part 132b of the resonance plate 132, is not reduced. Meanwhile, due to the deformation of the resonance plate 132, the volume of the first chamber 130 is shrunken and a middle communication space of the first chamber 130 is closed. Under this circumstance, the pressure gradient occurs to push the fluid in the first chamber 130 moving toward peripheral regions of the first chamber 130 and flowing downwardly through the vacant space 1335 of the piezoelectric actuator 133.

Figure 6C:
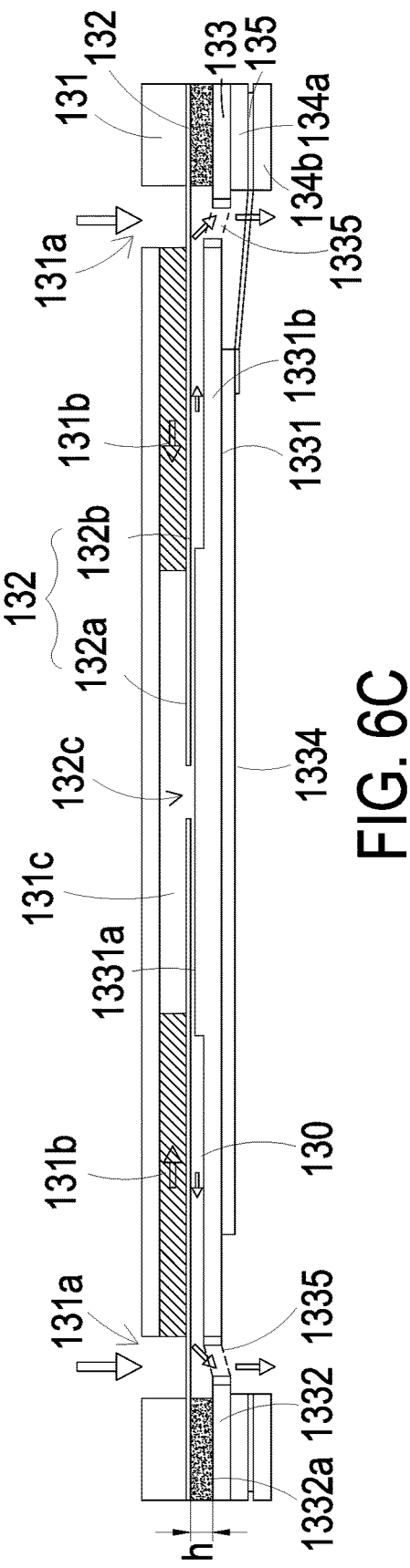

As shown in FIG. 6C, the movable part 132a of the resonance plate 132 is undergoing bending vibration and bends upwardly in vibration to return to its original position. At the same time, the piezoelectric actuator 133 vibrates upwardly and consequently compresses the volume of the first chamber 130, making the fluid in the first chamber 130 flow toward peripheral regions. Meanwhile, the external ambient fluid is continuously fed into the at least one inlet 131a of the fluid inlet plate 131, and transferred to the central cavity 131c.

Then, as shown in FIG. 6D, the movable part 132a of the resonance plate 132 moves upwardly, which is cause by the resonance of the upward motion of the piezoelectric actuator 133. Consequently, the fluid is restrained from flowing into the at least one inlet 131a of the fluid inlet plate 131 and being transferred to the central cavity 131c.

Afterwards, as shown in FIG. 6E, the movable part 132a of the resonance plate 132 returns to its original position. According to the aspect mentioned above, when the resonance plate 132 is vibrating along the vertical direction in the reciprocating manner, the gap h between the resonance plate 132 and the piezoelectric actuator 133 can increase maximum distance of vertical displacement of the resonance plate 132. That is, the depth of the gap h between the resonance plate 132 and the piezoelectric actuator 133 facilitates larger magnitude of upward and downward displacement of the resonance plate 132 in the resonance. Consequently, a pressure gradient is generated in the designed fluid channels of the fluid actuating device 13 to facilitate the fluid to flow at a high speed. Moreover, since there is an impedance difference between the feeding direction and the exiting direction, the fluid can be transmitted from the inlet side to the outlet side and fluid transportation is consequently achieved. Moreover, even if the outlet side has a gas pressure, the fluid actuating device 13 still has the capability of pushing the fluid to the fluid channels as well as achieving the silent efficacy.

The steps of FIGS. 6A to 6E are repeatedly done. Consequently, the ambient fluid is transferred by the fluid actuating device 13 from the outside to the inside.

After the fluid inlet plate 131, the resonance plate 132, the piezoelectric actuator 133, the first insulation plate 134a, the conducting plate 135 and the second insulation plate 134b are stacked on each other sequentially, the fluid actuating device 13 is assembled. The fluid actuating device 13 is disposed on the carrier 11 with a fluid channel (not shown) retained between the fluid actuating device 13 and the carrier 11. The fluid channel is arranged beside a lateral side of the sensor 12. When the fluid actuating device 13 is enabled, the fluid is compressed to flow out through the fluid channel and thus passing through the fluid channel and being sensed by the sensor 12. Since the fluid is guided to the sensor 12 by the fluid actuating device 13 at a stable flowrate, the sensor 12 can monitor the fluid to acquire the accurate result. In addition, since the response time of the sensor 12 is reduced, the efficiency of monitoring the fluid is enhanced.

Moreover, the data transceiver 16 can receive a control command to activate the sensor 12 and the actuating device 13. In addition, the data transceiver 16 can transmit an output data generated by the monitored data to the connection device 3 for displaying, storing or transmitting the output data thereby. Consequently, the purpose of immediately displaying the output data and issuing the notification signal are achieved. Moreover, the output data can be transmitted to a cloud database. Consequently, the purpose of constructing and managing the data can be achieved. Accordingly, an air quality notification mechanism and an air quality processing mechanism are enabled.

Please refer to FIG. 1B. FIG. 1B schematically illustrates the architecture of an information transmitting system for an actuating and sensing module according to a second embodiment of the present disclosure. In this embodiment, the actuating and sensing device 1 is not equipped with a power source, but the information transmitting system for the actuating and sensing module further includes a power supply device 2 to transfer the energy to power the sensor and the actuating device 1. Since the installation space of the overall modular structure is saved, the purpose of minimizing the modular structure is achieved, and the modular structure is suitably applied to an electronic device for monitoring the air quality. The actuating and sensing device 1 further includes a power controller 15. The power supply device 2 transfers the energy to the power controller 15. After the power controller 15 receives the energy, the power controller 15 enables the sensor 12 and the actuating device 13. In some embodiments, the energy includes but not limited to a light energy, an electric energy, a magnetic energy, a sound energy or a chemical energy.

In an embodiment, the power supply device 2 transfers the energy to the power controller 15 according to a wired transmission technology. For example, the power supply device 2 is a charger or a rechargeable battery, and the power supply device 2 transfers the energy to the power controller 15 according to the wired transmission technology. In another embodiment, the power supply device 2 transfers the energy to the power controller 15 according to a wireless transmission technology. For example, the power supply device 2 is a charger or a rechargeable battery equipped with a wireless charging component (or an inductive charging component) for transferring the energy to the power controller 15 according to the wireless transmission technology. In another embodiment, the power supply device 2 is a portable electronic device with wireless charging/discharging capability (e.g., a smart phone). For example, the smart phone has a wireless charging component (or an inductive charging component), and the smart phone transfers the energy to the power controller 15 according to the wireless transmission technology.

In an embodiment, the power controller 15 further includes a chargeable element (not shown) for receiving and storing the energy. The chargeable element of the power controller 15 receives the energy from the power supply device 2 transferred through a wired transmission path or a wireless transmission path. Then, the chargeable element stores the energy, and outputs the energy to the sensor 12 and the actuating device 13 for powering the sensor 12 to perform a sensing operation and powering the actuating device 13.

From the above descriptions, the present disclosure provides an information transmitting system for an actuating and sensing module. The system includes an actuating and sensing device and a connection device. The actuating and sensing device includes at least one sensor, at least one actuating device, a microprocessor and a data transceiver. The at least one sensor, the at least one actuating device, the microprocessor and the data transceiver are integrated as a modular structure. The actuating device drives the fluid to flow at high speed and provides stable fluid flow in consistent amount to the sensor. Consequently, the sensor can monitor the fluid directly and the response time of the sensor is reduced, so that precise detection is achieved. Moreover, the actuating and sensing device receives a control command through a data transceiver and accordingly controls the sensing operation of the sensor and the actuating operation of the actuating device. After a monitored data sensed by the at least one sensor is transmitted to the microprocessor, the monitored data is processed into an output data. The output data is transmitted to the connection device by the data receiver, so that the information carried by the output data can be displayed, stored and transmitted by the connection device. Consequently, the purpose of immediately displaying the monitoring information and immediately issuing the notification signal are achieved. Moreover, the output data can be transmitted to a cloud database for database construction and data integration. Consequently, the more immediate and accurate air quality information is provided for enabling an air quality notification mechanism and an air quality processing mechanism. In addition, the actuating and sensing device is not necessarily equipped with a power source since it is in connection with the power supply device. The power supply device transfers the energy to a power controller of the actuating and sensing device, so that the sensor and the actuating device are powered. Therefore, the installation space of the overall modular structure is saved, and the purpose of minimizing the modular structure is achieved, so that the actuating and sensing device is suitably applied to an electronic device for monitoring the air quality.

While the disclosure has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. An information transmitting system for an actuating and sensing module, comprising:
   a miniature actuating and sensing device comprising at least one sensor, at least one piezoelectric pump, a microprocessor and a data transceiver integrated as a modular structure; and
   a connection device,
   wherein after a monitored data sensed by the at least one sensor is transmitted to the microprocessor, the monitored data is processed into an output data by the microprocessor, wherein the output data is received by the data transceiver, and the output data is transmitted from the data transceiver to the connection device, wherein a control command from the connection device is received by the data transceiver, and the control command is transmitted to the microprocessor to enable the at least one sensor to perform a sensing operation and enable the at least one piezoelectric pump,
   wherein the piezoelectric pump comprises:
      a fluid inlet plate having at least one inlet, at least one convergence channel and a central cavity, wherein a convergence chamber is defined by the central cavity, and the at least one convergence channel spatially corresponds to the at least one inlet, wherein after a fluid is introduced into the at least one convergence channel through the at least one inlet, the fluid is guided by the at least one convergence channel and converged to the convergence chamber;
      a resonance plate having a central aperture, wherein the central aperture is spatially corresponding to the convergence chamber, wherein the resonance plate comprises a movable part around the central aperture; and
      a piezoelectric actuator spatially corresponding to the resonance plate, wherein a gap is formed between the resonance plate and the piezoelectric actuator to define a first chamber, wherein when the piezoelectric actuator is enabled, the fluid is fed into the piezoelectric pump through the at least one inlet of the fluid inlet plate, converged to the central cavity through the at least one convergence channel, transferred through the central aperture of the resonance plate, and introduced into the first chamber, wherein the fluid is transferred through a resonance between the piezoelectric actuator and the movable part of the resonance plate.

2. The information transmitting system for the actuating and sensing module according to claim 1, wherein the connection device is configured to display, store and transmit the output data.

3. The information transmitting system for the actuating and sensing module according to claim 1, wherein the connection device is connected with a notification processing system to enable an air quality notification mechanism.

4. The information transmitting system for the actuating and sensing module according to claim 1, wherein the connection device is connected with a notification processing device to enable an air quality processing mechanism.

5. The information transmitting system for the actuating and sensing module according to claim 2, wherein the connection device is a display device with a wired communication module or a display device with a wireless communication module.

6. The information transmitting system for the actuating and sensing module according to claim 2, wherein the connection device is a portable mobile device with a wireless communication module.

7. The information transmitting system for the actuating and sensing module according to claim 2, further comprising a networking relay station, wherein the output data is transmitted from the connection device to the networking relay station.

8. The information transmitting system for the actuating and sensing module according to claim 7, further comprising a cloud data processor, wherein after the output data is transmitted from the networking relay station to the cloud data processor, the output data is processed by and stored in the cloud data processor.

9. The information transmitting system for the actuating and sensing module according to claim 8, wherein after the output data is processed by the cloud data processor, the cloud data processor issues a notification signal to the networking relay station and then the notification signal is transmitted to the connection device, wherein the connection device is connected with a notification processing system to enable an air quality notification mechanism.

10. The information transmitting system for the actuating and sensing module according to claim 8, wherein after the output data is processed by the cloud data processor, the cloud data processor issues a notification signal to the networking relay station and then the notification signal is transmitted to the connection device, wherein the connection device is connected with a notification processing device to enable an air quality processing mechanism.

11. The information transmitting system for the actuating and sensing module according to claim 9, wherein the connection device is a display device with a wired communication module or a display device with a wireless communication module.

12. The information transmitting system for the actuating and sensing module according to claim 9, wherein the connection device is a portable mobile device with a wireless communication module.

13. The information transmitting system for the actuating and sensing module according to claim 8, further comprising a second connection device, wherein after the second connection device issues a control command to the cloud data processor through the networking relay station, the control command is transmitted from the cloud data processor to the connection device through the networking relay station, so that the connection device issues the control command to the data transceiver.

14. The information transmitting system for the actuating and sensing module according to claim 13, wherein the second connection device is a device with a wired communication module or a device with a wireless communication module.

15. The information transmitting system for the actuating and sensing module according to claim 13, wherein the second connection device is a portable mobile device with a wireless communication module.

16. The information transmitting system for the actuating and sensing module according to claim 1, wherein the sensor comprises at least one selected from the group consisting of an oxygen sensor, a carbon monoxide sensor, a carbon dioxide sensor, a gas sensor, a temperature sensor, a liquid sensor, a humidity sensor, an ozone sensor, a particulate sensor, a volatile organic compound sensor and a light sensor.

17. The information transmitting system for the actuating and sensing module according to claim 1, wherein the piezoelectric pump is a MEMS pump.

18. The information transmitting system for the actuating and sensing module according to claim 1, wherein the piezoelectric actuator comprises:
   a suspension plate being a square suspension plate and having a first surface and an opposing second surface, wherein the suspension plate is permitted to undergo a bending vibration;
   an outer frame arranged around the suspension plate;
   at least one bracket connected between the suspension plate and the outer frame for elastically supporting the suspension plate; and
   a piezoelectric plate, wherein a length of a side of the piezoelectric plate is smaller than or equal to a length of a side of the suspension plate, and the piezoelectric plate is attached on the first surface of the suspension plate, wherein when a voltage is applied to the piezoelectric plate, the suspension plate is driven to undergo the bending vibration.

19. An information transmitting system for an actuating and sensing module, comprising:
   at least one miniature actuating and sensing device comprising at least one sensor, at least one piezoelectric pump, at least one microprocessor and at least one data transceiver integrated as a modular structure; and
   at least one connection device,
   wherein after a monitored data sensed by the sensor is transmitted to the microprocessor, the monitored data is processed into at least one output data by the microprocessor, wherein the output data is received by the data transceiver, and the output data is transmitted from the data transceiver to the connection device, wherein at least one control command from the connection device is received by the data transceiver, and the control command is transmitted to the microprocessor to enable the sensor to perform a sensing operation and enable the piezoelectric pump,
   wherein the piezoelectric pump comprises:
      a fluid inlet plate having at least one inlet, at least one convergence channel and a central cavity, wherein a convergence chamber is defined by the central cavity, and the at least one convergence channel spatially corresponds to the at least one inlet, wherein after a fluid is introduced into the at least one convergence channel through the at least one inlet, the fluid is guided by the at least one convergence channel and converged to the convergence chamber;
      a resonance plate having a central aperture, wherein the central aperture is spatially corresponding to the convergence chamber, wherein the resonance plate comprises a movable part around the central aperture; and
      a piezoelectric actuator spatially corresponding to the resonance plate, wherein a gap is formed between the resonance plate and the piezoelectric actuator to define a first chamber, wherein when the piezoelectric actuator is enabled, the fluid is fed into the piezoelectric pump through the at least one inlet of the fluid inlet plate, converged to the central cavity through the at least one convergence channel, transferred through the central aperture of the resonance plate, and introduced into the first chamber, wherein the fluid is transferred through a resonance between the piezoelectric actuator and the movable part of the resonance plate.

* * * * *